United States Patent
Kimura

(10) Patent No.: US 7,812,955 B2
(45) Date of Patent: Oct. 12, 2010

(54) SAMPLE ANALYSIS APPARATUS AND ANALYSIS METHOD

(75) Inventor: Toshihito Kimura, Kanagawa-ken (JP)

(73) Assignee: FUJIFILM Corporation (JP)

( * ) Notice: Subject to any disclaimer, the term of this patent is extended or adjusted under 35 U.S.C. 154(b) by 406 days.

(21) Appl. No.: 11/194,694

(22) Filed: Aug. 2, 2005

(65) Prior Publication Data

US 2006/0023221 A1    Feb. 2, 2006

(30) Foreign Application Priority Data

Aug. 2, 2004    (JP) ............................. 2004-225522

(51) Int. Cl.
    *G01N 21/55* (2006.01)

(52) U.S. Cl. ..................................... 356/445

(58) Field of Classification Search ................. 356/445
See application file for complete search history.

(56) References Cited

U.S. PATENT DOCUMENTS

| | | | |
|---|---|---|---|
| 4,429,218 A * | 1/1984 | Thomas ................. 250/214 R |
| 4,668,044 A * | 5/1987 | D'Auria et al. ............... 385/92 |
| 4,997,278 A | 3/1991 | Finlan et al. |
| 5,245,410 A * | 9/1993 | Villuendas Yuste et al. . 356/445 |
| 5,508,809 A * | 4/1996 | Peacock et al. ............. 356/445 |
| 5,875,032 A | 2/1999 | Naya |
| 5,912,456 A | 6/1999 | Melendez |
| 5,923,031 A | 7/1999 | Naya |
| 6,111,652 A * | 8/2000 | Melendez et al. ........... 356/445 |
| 2004/0130723 A1* | 7/2004 | Yager et al. ................. 356/445 |

FOREIGN PATENT DOCUMENTS

| | | |
|---|---|---|
| EP | 0834848 A2 | 8/1998 |
| JP | 1138443 A | 5/1989 |
| JP | 6-167443 A | 6/1994 |
| JP | 9292334 A | 11/1997 |
| JP | 10206318 A | 8/1998 |
| JP | 10-239233 A | 9/1998 |
| JP | 11051857 A | 2/1999 |
| JP | 2000356586 A | 12/2000 |
| JP | 2001041881 A | 2/2001 |
| JP | 2003139692 A | 5/2003 |
| JP | 2004053372 A | 2/2004 |

OTHER PUBLICATIONS

Takayuki Okamoto, "Surface Refracto-Sensor using Evanescent Waves: Principles and Instrumentations", Spectrum Researches, pp. 19-28, vol. 47, No. 1.

* cited by examiner

*Primary Examiner*—Gregory J. Toatley, Jr.
*Assistant Examiner*—Juan D Valentin
(74) *Attorney, Agent, or Firm*—Sughrue Mion, PLLC

(57) ABSTRACT

A light beam irradiating optical system is associated with a dielectric material member having a surface, on which a thin film layer has been formed, a sample being brought into contact with a surface of the thin film layer. The light beam irradiating optical system produces and irradiates a light beam to an interface between the dielectric material member and the thin film layer. The light beam is constituted of light beam components, which have various different incidence angles with respect to the interface, and which have intensities varying in accordance with the incidence angles. A single measuring detector for outputting a signal representing an intensity of an entire area of received light is secured and located so as to receive the light beam having been reflected from the interface.

26 Claims, 8 Drawing Sheets

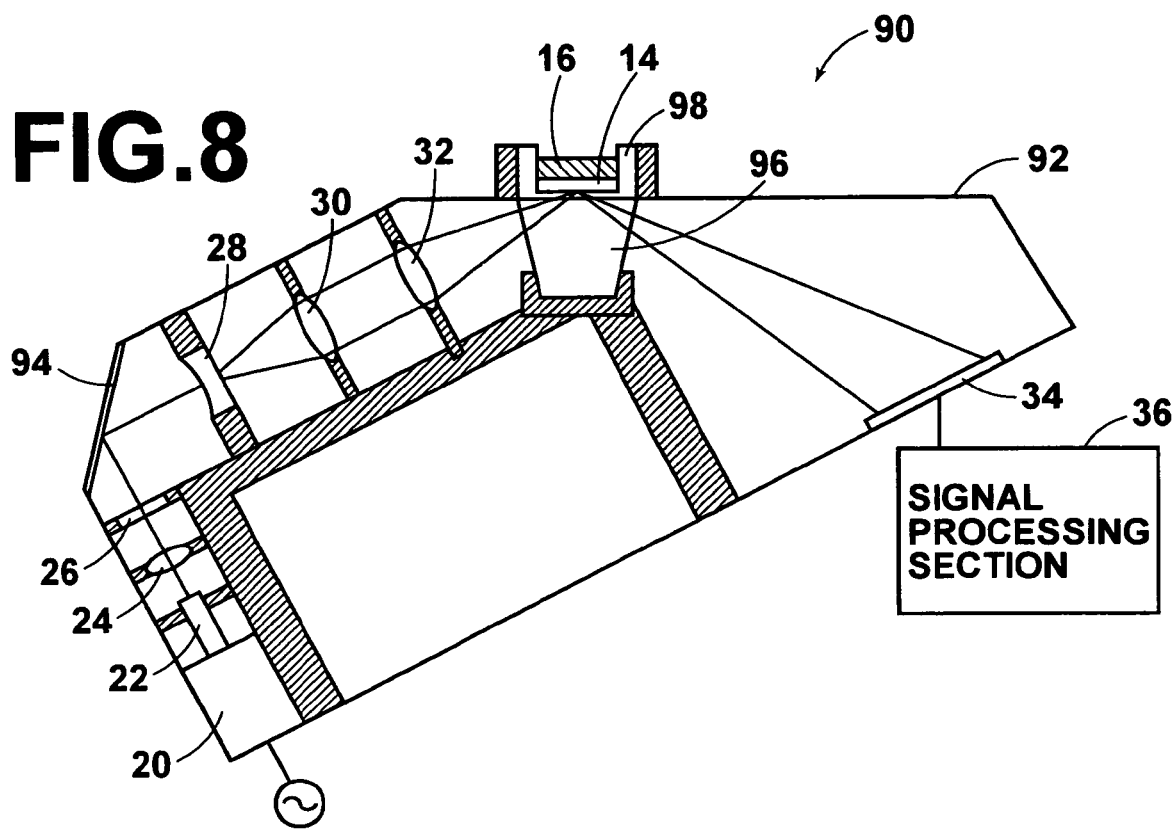

SAMPLE ANALYSIS APPARATUS AND ANALYSIS METHOD

BACKGROUND OF THE INVENTION

1. Field of the Invention

This invention relates to a sample analysis apparatus and an analysis method. This invention particularly relates to a sample analysis apparatus, wherein a light beam is reflected from an interface between a thin film layer, which is in contact with a sample, and a dielectric material member, and an alteration occurring with an intensity of the reflected light beam is measured for an analysis of the sample. Also, this invention particularly relates to an analysis method, wherein an attenuated total reflection angle of the sample is measured by use of the sample analysis apparatus.

2. Description of the Related Art

As sample analysis apparatuses utilizing evanescent waves, surface plasmon sensors have heretofore been known. In metals, free electrons vibrate collectively, and a compression wave referred to as a plasma wave is thereby produced. The compression wave occurring on the metal surface and having been quantized is referred to as the surface plasmon. With the surface plasmon sensors, characteristics of samples are analyzed by the utilization of a phenomenon, in which the surface plasmon is excited by a light wave. Various types of surface plasmon sensors have heretofore been proposed. As one of well known surface plasmon sensors, a surface plasmon sensor utilizing a system referred to as the Kretschman arrangement may be mentioned. The surface plasmon sensor utilizing the system referred to as the Kretschman arrangement is described in, for example, Japanese Unexamined Patent Publication No. 6(1994)-167443.

Ordinarily, the surface plasmon sensor utilizing the system referred to as the Kretschman arrangement comprises (i) a dielectric material member having, for example, a prism-like shape, (ii) a metal film, which is formed on one surface of the dielectric material member and is brought into contact with a sample, (iii) a light beam irradiating optical system for producing a light beam and irradiating the light beam to an interface between the dielectric material member and the metal film at various different incidence angles such that a total reflection condition may be obtained at the interface between the dielectric material member and the metal film, and (iv) a detector for detecting the intensity of the light beam, which has been totally reflected from the interface described above.

With the surface plasmon sensor having the constitution described above, in cases where the light beam impinges at a specific incidence angle $\theta_{SP}$, which is not smaller than the total reflection angle, upon the metal film, an evanescent wave having an electric field distribution occurs in the sample, which is in contact with the metal film, and the surface plasmon is excited by the evanescent wave and at the interface between the metal film and the sample. In cases where the wave vector of the evanescent wave coincides with the wave vector of the surface plasmon, and wave number matching is thus obtained, the evanescent wave and the surface plasmon resonate. (The thus occurring resonance is referred to as the surface plasmon resonance.) Energy of the light thus transfers to the surface plasmon. As a result, the intensity of the reflected light beam, which is totally reflected from the interface between the dielectric material member and the metal film, becomes markedly low. (The phenomenon, in which the intensity of the reflected light beam thus becomes markedly low, is referred to as the attenuated total reflection.) Ordinarily, the lowering of the intensity of the reflected light beam is detected as a dark line by the detector described above.

The surface plasmon resonance described above occurs only in cases where the incident light beam is a P-polarized light beam. Therefore, it is necessary for the incident light beam to be set previously so as to impinge upon the aforesaid interface as the P-polarized light beam.

The specific incidence angle $\theta_{SP}$, which is associated with the lowering of the intensity of the reflected light beam, will hereinbelow be referred to as the attenuated total reflection angle (ATR angle) $\theta_{SP}$. In cases where the wave number of the surface plasmon is found from the ATR angle $\theta_{SP}$, a dielectric constant of the sample is capable of being calculated. Specifically, the formula shown below obtains.

$$K_{SP}(\omega) = \frac{\omega}{c} \sqrt{\frac{\varepsilon_m(\omega)\varepsilon_s}{\varepsilon_m(\omega) + \varepsilon_s}}$$

wherein $K_{SP}$ represents the wave number of the surface plasmon, $\omega$ represents the angular frequency of the surface plasmon, $c$ represents the light velocity in a vacuum, $\in_m$ represents the dielectric constant of the metal, and $\in_s$ represents the dielectric constant of the sample.

Specifically, in cases where the dielectric constant $\in_s$ of the sample is found, the refractive index of the sample, or the like, is capable of being found in accordance with a predetermined calibration curve, or the like. Therefore, in cases where the ATR angle $\theta_{SP}$ is found, the dielectric constant $\in_s$ of the sample is capable of being calculated. Accordingly, the characteristics with regard to the refractive index of the sample are capable of being calculated.

Besides the surface plasmon sensor, as a similar sensor utilizing the evanescent wave, a leaky mode sensor has heretofore been known. (The leaky mode sensor is described in, for example, "Surface Refracto-Sensor using Evanescent Waves: Principles and Instrumentations" by Takayuki Okamoto, Spectrum Researches, Vol. 47, No. 1, 1998.) Basically, the leaky mode sensor comprises (i) a dielectric material member having, for example, a prism-like shape, (ii) a cladding layer, which is formed on one surface of the dielectric material member, (iii) an optical waveguide layer, which is formed on the cladding layer and is brought into contact with a sample, (iv) a light beam irradiating optical system for producing a light beam and irradiating the light beam to an interface between the dielectric material member and the cladding layer at various different incidence angles such that a total reflection condition may be obtained at the interface between the dielectric material member and the cladding layer, and (v) a detector for detecting the intensity of the light beam, which has been totally reflected from the interface described above. The state of excitation of a guided mode is specified in accordance with the result of the detection having been made by the detector, and an analysis of the sample is thereby made.

With the leaky mode sensor having the constitution described above, in cases where the light beam impinges at an incidence angle, which is not smaller than the total reflection angle, upon the cladding layer via the dielectric material member, only the light having a certain specific wave number, which light has impinged at a specific incidence angle upon the cladding layer, is propagated in the guided mode in the optical waveguide layer after passing through the cladding layer. In cases where the guided mode is thus excited, approximately all of the incident light is taken into the optical waveguide layer, and the attenuated total reflection thus occurs. Also, the wave number of the guided optical wave depends upon the refractive index of the sample, which is located on the optical waveguide layer. Therefore, in cases where the ATR angle $\theta_{SP}$ is detected, the refractive index of the sample and characteristics of the sample with regard to the refractive index of the sample are capable of being analyzed.

In the fields of pharmaceutical research, and the like, the surface plasmon sensor and the leaky mode sensor described above are often utilized for random screening for finding out a specific substance, which is capable of undergoing the binding with a desired sensing substance. In such cases, the sensing substance is fixed to the aforesaid thin film layer (the metal film in the cases of the surface plasmon sensor, or the combination of the cladding layer and the optical waveguide layer in the cases of the leaky mode sensor), and a liquid (a liquid sample) containing a test body is introduced on the sensing substance. Also, at each of stages after the passage of predetermined periods of time, the aforesaid ATR angle $\theta_{SP}$ is measured.

In cases where the test body contained in the liquid sample is a substance capable of undergoing the binding with the sensing substance, the refractive index of the sensing substance alters with the passage of time. Therefore, the aforesaid ATR angle $\theta_{SP}$ is measured at each of stages after the passage of predetermined periods of time, and a judgment is made as to whether an alteration of the ATR angle $\theta_{SP}$ has been or has not been occurred. In this manner, a judgment is capable of being made as to whether the binding of the test body with the sensing substance has or has not occurred, i.e. as to whether the test body is or is not the specific substance capable of undergoing the binding with the sensing substance. Examples of the combinations of the specific substances and the sensing substances include the combination of an antigen and an antibody and the combination of an antibody and a different antibody. Specifically, examples of the analyses with regard to the combinations of the specific substances and the sensing substances include an analysis, wherein a rabbit anti-human IgG antibody is employed as the sensing substance, a detection is made as to whether a human IgG antibody acting as the test body has or has not been bound to the rabbit anti-human IgG antibody, and a quantitative analysis of the human IgG antibody is made.

In order for the state of the binding of the test body, which is contained in the liquid sample, with the sensing substance to be detected, the ATR angle $\theta_{SP}$ itself need not necessarily be detected. Alternatively, for example, the liquid sample containing the test body may be introduced onto the sensing substance, and thereafter the quantity of the alteration of the ATR angle $\theta_{SP}$ may be measured. Also, the state of the binding of the test body with the sensing substance may be detected in accordance with the quantity of the alteration of the ATR angle $\theta_{SP}$.

As a technique for obtaining the various different incidence angles described above in each of the surface plasmon sensor and the leaky mode sensor, there has been known a technique, wherein a light beam having a small beam diameter is successively caused to impinge upon the aforesaid interface with the incidence angle being altered. (The aforesaid technique for obtaining the various different incidence angles is described in, for example, Japanese Unexamined Patent Publication No. 10(1998)-239233.) In such cases, the reflected light beam, which is reflected from the interface with its reflection angle altering in accordance with the alteration of the incidence angle of the incident light beam, may be detected with a small single-cell type of detector, which moves by being interlocked with the alteration of the reflection angle. Alternatively, the reflected light beam may be detected with a single-cell type of detector or a multi-cell type of detector, which extends in the direction of alteration of the reflection angle. In this manner, the incidence angle at the time at which the dark line is detected is capable of being specified as the attenuated total reflection angle.

As a different technique for obtaining the various different incidence angles described above in each of the surface plasmon sensor and the leaky mode sensor, there has been known a technique, wherein a light beam, which has a large beam diameter and is constituted of light beam components having various different incidence angles, is caused to impinge upon the aforesaid interface in a state of converged light or in a state of divergent light. (The aforesaid different technique for obtaining the various different incidence angles is described in, for example, Japanese Unexamined Patent Publication Nos. 6(1994)-167443 and U.S. Pat. No. 5,912,456.) In such cases, the light beam components, which have been reflected from the interface at various different reflection angles, may be detected with a multi-cell type of line sensor or a two-dimensional array sensor, which extends in a direction such that the sensor is capable of receiving all of the light beam components having been reflected from the interface at various different reflection angles. In this manner, the incidence angle of a light beam component corresponding to the position, at which the dark line has been detected, is capable of being specified as the attenuated total reflection angle.

However, with the technique, wherein the light beam having the small beam diameter is successively caused to impinge upon the aforesaid interface with the incidence angle being altered, the problems are encountered in that the constitution for altering the incidence angle is not capable of being kept simple, and in that quick processing is not capable of being performed. Also, in cases where the incidence angle is altered by use of a mechanical movement mechanism, the problems occur in that the detection accuracy is limited by an angle setting accuracy of the movement mechanism.

Also, with the technique, wherein the light beam, which has the large beam diameter and is constituted of the light beam components having various different incidence angles, is caused to impinge upon the aforesaid interface in the state of converged light or in the state of divergent light, the problems are encountered in that it is necessary for the detector whose cost is high, such as the multi-cell type of the line sensor or the two-dimensional array sensor, to be utilized, and in that calculation processing with complicated algorithms is required for the detection of the position of the dark line. Further, the problems occur in that the accuracy, with which the position of the dark line is detected, is limited due to adverse effects of unevenness of the interface and a spread width of the dark line. (particularly, in cases where a light source other than a laser beam is utilized).

SUMMARY OF THE INVENTION

The primary object of the present invention is to provide a sample analysis apparatus, wherein an alteration occurring with an intensity of a reflected light beam that has been reflected from an interface between a thin film layer, which is in contact with a sample, and a dielectric material member, is capable of being measured with respect to various different incidence angles and quickly by use of a low-cost, simple apparatus constitution.

Another object of the present invention is to provide an analysis method, wherein an attenuated total reflection angle of a sample is measured by use of the sample analysis apparatus and with simple calculation processing.

The present invention provides a sample analysis apparatus, comprising:

i) a light beam irradiating optical system associated with a dielectric material member having a surface, on which a thin film layer has been formed, a sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, and ii) a single measuring detector for outputting a signal, which represents an intensity of an entire area of light received by the measuring detector, the measuring detector being secured and located such that the measuring detector is capable of receiving the light beam, which has been reflected from the interface between the dielectric material member and the thin film layer.

In the sample analysis apparatus in accordance with the present invention, the single measuring detector for outputting the signal, which represents the intensity of the entire area of the light received by the measuring detector, may be a single-cell type of detector. Alternatively, the single measuring detector may be a multi-cell type of detector, such as a CCD sensor, which is utilized so as to output an integration signal representing the total intensity of the light received by all of the cells.

Also, in the sample analysis apparatus in accordance with the present invention, the measuring detector is secured and located such that the measuring detector is capable of receiving the light beam, which has been reflected from the interface between the dielectric material member and the thin film layer. Specifically, the measuring detector may be secured and located such that the measuring detector is capable of receiving the entire area of the light beam, which has been reflected from the interface between the dielectric material member and the thin film layer. Alternatively, the measuring detector may be secured and located such that the measuring detector is capable of receiving only part of the light beam having been reflected from the interface between the dielectric material member and the thin film layer, which part contains the light beam components having reflection angles falling within a desired range (i.e., having incidence angles falling within a desired range).

The sample analysis apparatus in accordance with the present invention may be modified such that the light beam irradiating optical system is provided with means for altering the range of the incidence angles, which the light beam embraces.

Also, the sample analysis apparatus in accordance with the present invention may be modified such that the light beam irradiating optical system is provided with means for altering a beam diameter of the entire area of the light beam.

Further, the sample analysis apparatus in accordance with the present invention may be modified such that the light beam, which is produced by the light beam irradiating optical system, has beam cross-sectional intensities, which monotonously increase or monotonously decrease in accordance with the incidence angles, in an incidence plane of a middle beam of the light beam with respect to the interface between the dielectric material member and the thin film layer.

Furthermore, the sample analysis apparatus in accordance with the present invention may be modified such that the light beam irradiating optical system produces the light beam by producing a beam, which has a Gaussian beam cross-sectional intensity distribution in a plane parallel with an incidence plane of a middle beam of the light beam with respect to the interface between the dielectric material member and the thin film layer, and converging or diverging the beam toward the interface between the dielectric material member and the thin film layer.

In such cases, the sample analysis apparatus in accordance with the present invention may further be modified such that the measuring detector is located so as to receive only a region of the light beam having been reflected from the interface between the dielectric material member and the thin film layer, which region corresponds to one side of the Gaussian beam cross-sectional intensity distribution. The term "region corresponding to one side of a Gaussian beam cross-sectional intensity distribution" as used herein means the region contained in one of two subdivisions, into which the Gaussian beam cross-sectional intensity distribution is divided at an intensity peak position.

Also, the sample analysis apparatus in accordance with the present invention may be modified such that the light beam irradiating optical system and the measuring detector are secured and located within a housing, and a sample support section, which comprises the dielectric material member and the thin film layer, is formed at a first surface of the housing, such that the thin film layer is exposed to the exterior of the housing.

In such cases, the sample analysis apparatus in accordance with the present invention should preferably be modified such that the light beam irradiating optical system comprises a light source section, and the light source section and the measuring detector are secured and located on a second surface within the housing, which second surface is different from the first surface of the housing.

Also, in such cases, the sample support section may be combined with the housing into an integral body. Alternatively, part of the sample support section or the whole of the sample support section may be releasable from the housing.

In cases where the measuring detector is located so as to receive only the region of the light beam having been reflected from the interface between the dielectric material member and the thin film layer, which region corresponds to one side of the Gaussian beam cross-sectional intensity distribution, the sample analysis apparatus in accordance with the present invention may further be modified such that the apparatus further comprises a light intensity monitoring detector for detecting an intensity of the whole or part of a remaining region of the light beam having been reflected from the interface between the dielectric material member and the thin film layer, which remaining region is other than the region received by the measuring detector.

Further, the sample analysis apparatus in accordance with the present invention may be modified such that the light beam, which is produced by the light beam irradiating optical system, is constituted of a first polarized light beam and a second polarized light beam, which are mixed together in a predetermined ratio, and the apparatus further comprises:

a polarization beam splitter for splitting the light beam, which has been reflected from the interface between the dielectric material member and the thin film layer, into the first polarized light beam and the second polarized light beam, the polarization beam splitter being located such that only the first polarized light beam is received by the measuring detector, and a light intensity monitoring detector for detecting an intensity of the whole or part of the second polarized light beam.

Furthermore, the sample analysis apparatus in accordance with the present invention may be modified such that the light beam irradiating optical system, the measuring detector, and the light intensity monitoring detector are secured and located within a housing, and a sample support section, which comprises the dielectric material member and the thin film layer, is formed at a first surface of the housing, such that the thin film layer is exposed to the exterior of the housing.

In such cases, the sample analysis apparatus in accordance with the present invention should preferably be modified such that the light beam irradiating optical system comprises a light source section, and the light source section, the measuring detector, and the light intensity monitoring detector are secured and located on a second surface within the housing, which second surface is different from the first surface of the housing.

Also, in such cases, the sample support section may be combined with the housing into an integral body. Alternatively, part of the sample support section or the whole of the sample support section may be releasable from the housing.

The present invention also provides a first analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, and ii) a single measuring detector for outputting a signal, which represents an intensity of an entire area of light received by the measuring detector, the measuring detector being secured and located such that the measuring detector is capable of receiving the light beam, which has been reflected from the interface between the dielectric material member and the thin film layer, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, being thereby obtained, and c) specifying an incidence angle of a light beam component among the light beam components constituting the light beam, which light beam component has been subjected to attenuated total reflection, in accordance with a value of a difference signal representing a difference between the first measurement signal and the second measurement signal, the thus specified incidence angle being taken as the attenuated total reflection angle of the sample.

The present invention further provides a second analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam irradiating optical system producing the light beam by producing a beam, which has a Gaussian beam cross-sectional intensity distribution in a plane parallel with an incidence plane of a middle beam of the light beam with respect to the interface between the dielectric material member and the thin film layer, and converging or diverging the beam toward the interface between the dielectric material member and the thin film layer, ii) a single measuring detector for outputting a signal, which represents an intensity of an entire area of light received by the measuring detector, the measuring detector being secured and located such that the measuring detector is capable of receiving only a region of the light beam having been reflected from the interface between the dielectric material member and the thin film layer, which region corresponds to one side of the Gaussian beam cross-sectional intensity distribution, and iii) a light intensity monitoring detector for detecting an intensity of the whole or part of a remaining region of the light beam having been reflected from the interface between the dielectric material member and the thin film layer, which remaining region is other than the region received by the measuring detector, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, and a first monitoring signal, which represents the intensity of the entire area of the light received by the light intensity monitoring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, and a second monitoring signal, which represents the intensity of the entire area of the light received by the light intensity monitoring detector, being thereby obtained, and c) specifying an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

The present invention still further provides a third analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam, which is produced by the light beam irradiating optical system, being constituted of a first polarized light beam and a second polarized light beam, which are mixed together in a predetermined ratio, ii) a polarization beam splitter for splitting the light beam, which has been reflected from the interface between the dielectric material member and the thin film layer, into the first polarized light beam and the second polarized light beam, iii) a single measuring detector for outputting a signal, which represents an intensity of an entire area of light received by the measuring detector, the measuring detector being secured and located such that the measuring detector is capable of receiving only the first polarized light beam, and iv) a light intensity monitoring detector for detecting an intensity of the whole or part of the second polarized light beam, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, and a first monitoring signal, which represents the intensity of the entire area of the light received by the light intensity monitoring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, and a second monitoring signal, which represents the intensity of the entire area of the light received by the light intensity monitoring detector, being thereby obtained, and c) specifying an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

With the sample analysis apparatus in accordance with the present invention, the single measuring detector for outputting the signal, which represents the intensity of the entire area of the light received by the measuring detector, is secured and located such that the measuring detector is capable of receiving the light beam, which has been reflected from the interface between the dielectric material member and the thin film layer. Therefore, with the low-cost, simple apparatus constitution, with respect to the light beam constituted of the light beam components, which have various different incidence angles with respect to the interface between the dielectric material member and the thin film layer, and which have intensities varying in accordance with the incidence angles with respect to the interface, an alteration occurring with the intensity of the reflected light beam is capable of being detected quickly. In particular, as in the cases of the attenuated total reflection, in cases where the light beam component among the light beam components constituting the light beam, which light beam component has a specific incidence angle, is subjected to a predetermined proportion of attenuation, modulation, or the like, and the alteration occurring with the intensity of the reflected light beam is thus caused to occur, the quantity of the alteration of the intensity of the reflected light beam is capable of being measured by use of the aforesaid low-cost, simple apparatus constitution, and the incidence angle of the light beam component, which has been subjected to the attenuation, modulation, or the like, is capable of being specified quickly. An analysis of the sample is thus capable of being made.

With the sample analysis apparatus in accordance with the present invention, wherein the light beam irradiating optical system is provided with the means for altering the range of the incidence angles, which the light beam embraces, the quantity of the alteration of the intensity of the reflected light beam is capable of being measured with respect to a desired range of the reflection angles (i.e., a desired range of the incidence angles) in accordance with the sample to be analyzed, and an accurate analysis of the sample is capable of being made. For example, in cases where the attenuated total reflection angle of the sample is to be measured, the range of the incidence angles is capable of being set such that the range of the incidence angles may embrace a range of an expected attenuated total reflection angle, and an accurate measurement is thereby capable of being made.

Also, the sample analysis apparatus in accordance with the present invention may be modified such that the light beam irradiating optical system is provided with the means for altering the beam diameter of the entire area of the light beam. With the modification described above, in cases where an analysis is to be made with respect to the light beam components having the incidence angles falling within a wide range, the light beam having a large beam diameter is capable of being utilized. Further, in cases where an analysis is to be made with respect to the light beam components having the incidence angles falling within a narrow range, the light beam having a small beam diameter is capable of being utilized. For example, in cases where the attenuated total reflection angle of the sample is to be measured, the attenuated total reflection angle is capable of being specified approximately by use of the light beam having a large beam diameter, which light beam has a gentle beam cross-sectional intensity distribution, and thereafter the attenuated total reflection angle is capable of being measured accurately by use of the light beam having a small beam diameter, which light beam has a sharp beam cross-sectional intensity distribution.

Further, the sample analysis apparatus in accordance with the present invention may be modified such that the light beam, which is produced by the light beam irradiating optical system, has beam cross-sectional intensities, which monotonously increase or monotonously decrease in accordance with the incidence angles, in an incidence plane of a middle beam of the light beam with respect to the interface between the dielectric material member and the thin film layer. With the modification described above, as in the cases of the attenuated total reflection angle, in cases where the incidence angle of the light beam component, which has been subjected to the predetermined proportion of the attenuation, modulation, or the like, is to be specified, the incidence angle of the aforesaid light beam component is capable of being specified more easily.

Furthermore, the sample analysis apparatus in accordance with the present invention may be modified such that the light beam irradiating optical system produces the light beam by producing the beam, which has the Gaussian beam cross-sectional intensity distribution, and converging or diverging the beam toward the interface between the dielectric material member and the thin film layer. With the modification described above, the light beam constituted of the light beam components, which have correlations between the incidence angles and the intensities, is capable of being produced with the simple apparatus constitution.

In such cases, the sample analysis apparatus in accordance with the present invention may further be modified such that the measuring detector is located so as to receive only the region of the light beam having been reflected from the interface between the dielectric material member and the thin film layer, which region corresponds to one side of the Gaussian beam cross-sectional intensity distribution. With the modification described above, as in the cases of the attenuated total reflection angle, in cases where the incidence angle of the light beam component, which has been subjected to the predetermined proportion of the attenuation, modulation, or the like, is to be specified, the incidence angle of the aforesaid light beam component is capable of being specified more easily.

With the sample analysis apparatus in accordance with the present invention, wherein the apparatus further comprises the light intensity monitoring detector, it is possible to make a judgment as to whether the alteration of the intensity of the reflected light beam, which intensity is detected by the measuring detector, is due to the attenuation or modulation caused to occur by the sample, or is due to a fluctuation of power of the incident light beam. Therefore, the analysis is capable of being made more accurately.

With the sample analysis apparatus in accordance with the present invention, wherein the light beam irradiating optical system and the measuring detector (and the light intensity monitoring detector in cases where the light intensity monitoring detector is provided) are secured and located within the housing, the sample analysis apparatus becomes easy to process, and re-adjustments for alignment of optical devices need not be performed after the sample analysis apparatus has been moved to a different location.

With the sample analysis apparatus in accordance with the present invention, wherein the light source section of the light beam irradiating optical system and the measuring detector (and the light intensity monitoring detector in cases where the light intensity monitoring detector is provided) are secured and located on the identical surface within the housing, electric wiring and an interface, which are connected to the exterior of the housing, are capable of being collected on the identical surface. Therefore, the easiness of the processing of the sample analysis apparatus is capable of being enhanced even further.

With each of the first, second, and third analysis methods in accordance with the present invention, the cost of the sample analysis apparatus utilized is capable of being kept low, and the constitution of the sample analysis apparatus utilized is capable of being kept simple. Also, the calculation processing for specifying the attenuated total reflection angle is capable of being kept simple. Therefore, the measurement of the attenuated total reflection angle of the sample and the analysis of the sample are capable of being performed with the low-cost, low-load processing.

BRIEF DESCRIPTION OF THE DRAWINGS

FIG. 8 is a side view showing a housing provided with a surface plasmon sensor, which has a constitution similar to the constitution of the surface plasmon sensor of FIG. 1.

DESCRIPTION OF THE PREFERRED EMBODIMENTS

The present invention will hereinbelow be described in further detail with reference to the accompanying drawings.

Figure 1:
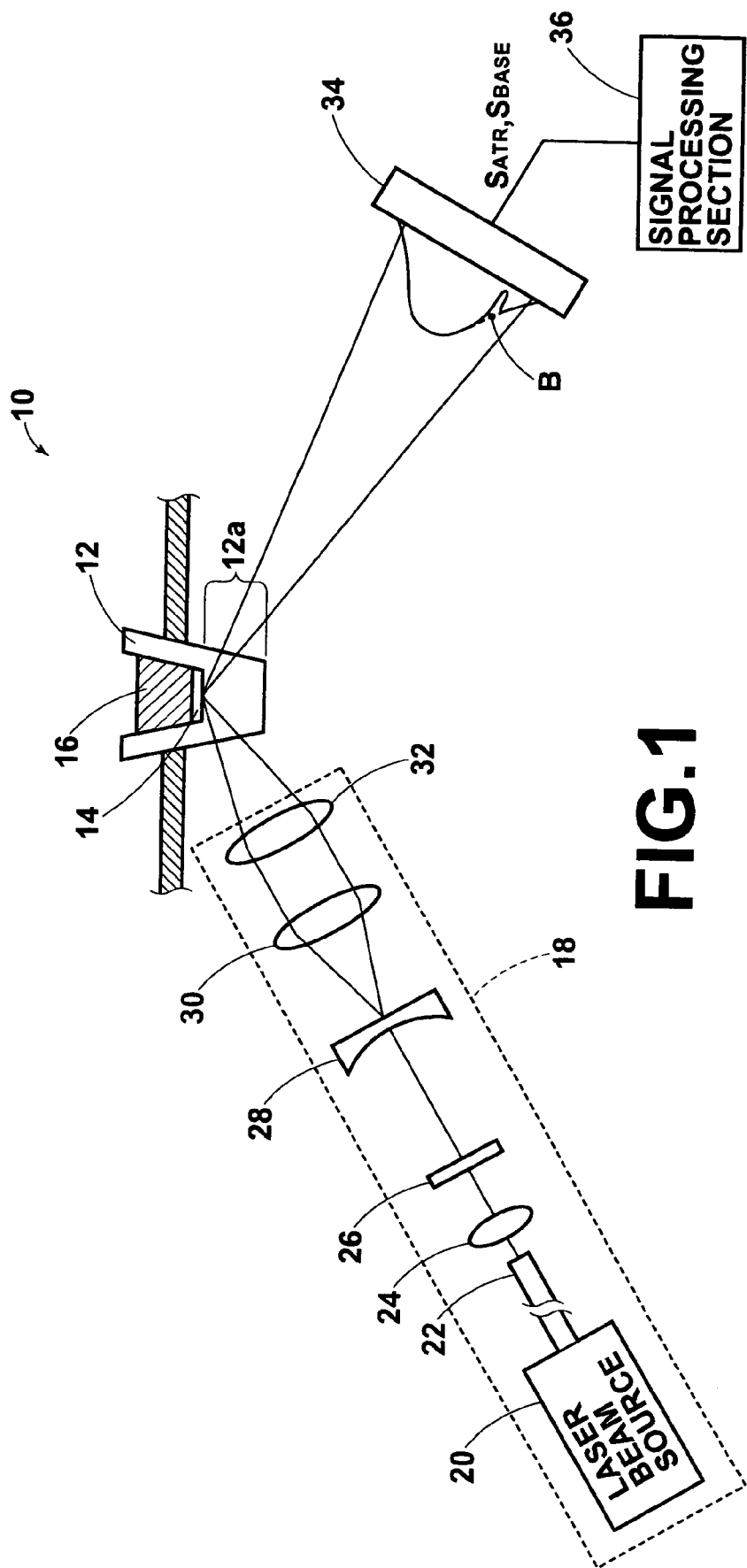
FIG. 1 is a side view showing a first embodiment of the sample analysis apparatus in accordance with the present invention, which is constituted as a surface plasmon sensor.

FIG. 1 is a side view showing a first embodiment of the sample analysis apparatus in accordance with the present invention, which is constituted as a surface plasmon sensor.

With reference to FIG. 1, a surface plasmon sensor 10 comprises a dielectric material member 12, which is releasable and exchangeable. The dielectric material member 12 has an approximately truncated quadrangular pyramid-like shape. An upper region of the dielectric material member 12 is formed into a cup-like shape. The dielectric material member 12 is constituted of a transparent resin, or the like. A lower region 12a of the dielectric material member 12 acts as a prism. A metal film 14 is formed on a bottom surface of the upper cup-shaped region of the dielectric material member 12. By way of example, the metal film 14 may be made from gold, silver, copper, aluminum, or the like. A liquid sample 16 is capable of being brought into contact with the metal film 14. In accordance with the kind of the liquid sample 16 and the purpose of analysis, a sensing substance (e.g., an antibody) may be fixed to the top surface of the metal film 14.

The surface plasmon sensor 10 also comprises a light beam irradiating optical system 18. The light beam irradiating optical system 18 produces a light beam and irradiates the light beam to an interface between the dielectric material member 12 and the metal film 14, i.e. to the bottom surface of the upper cup-shaped region of the dielectric material member 12. The light beam, which is produced by the light beam irradiating optical system 18, is constituted of light beam components, which have various different incidence angles with respect to the interface between the dielectric material member 12 and the metal film 14, and which have intensities varying in accordance with the incidence angles with respect to the interface. In this embodiment, the light beam irradiating optical system 18 comprises a laser beam source 20, a polarization plane keeping fiber 22, a collimator lens 24, a polarizing plate 26, a diverging lens 28, a converging lens 30, and a converging lens 32. The laser beam source 20 of the light beam irradiating optical system 18 produces a beam, which has a Gaussian beam cross-sectional intensity distribution. The beam having been produced by the laser beam source 20 is diverged and is then converged toward the interface described above. The aforesaid light beam (in this case, the laser beam) is thus irradiated to the interface described above. With the constitution described above, the laser beam impinging upon the interface described above contains the laser beam components, which have various different incidence angles θ with respect to the interface described above, and which have the intensities having a correlation (a Gaussian distribution correlation) with the incidence angles θ with respect to the interface. The incidence angles θ are set to be not smaller than the total reflection angle. In the embodiment of FIG. 1, the beam is converged so as to be focused upon the interface between the dielectric material member 12 and the metal film 14. Alternatively, the light beam irradiating optical system 18 may be constituted such that the laser beam impinges in a defocused state upon the interface described above. In such cases, errors in detection of the state of the surface plasmon resonance are capable of being averaged, and the analysis accuracy is capable of being enhanced.

The polarizing plate 26 extracts only the polarized light beam, i.e. the P-polarized light beam, which causes the surface plasmon resonance to occur, from the beam having been produced by the laser beam source 20.

The laser beam, which has been irradiated from the light beam irradiating optical system 18 toward the interface between the dielectric material member 12 and the metal film 14, is reflected from the interface and is then received by a single measuring detector 34, which is secured and located so as to receive the reflected laser beam. The measuring detector 34 outputs a signal, which represents an intensity of an entire area of light received by the measuring detector 34, into a signal processing section 36. The measuring detector 34 may be a single-cell type of detector. Alternatively, the measuring detector 34 may be a multi-cell type of detector, such as a CCD sensor, which is utilized so as to output an integration signal representing the total intensity of the light received by all of the cells.

How an analysis, in which an ATR angle $\theta_{SP}$ of the liquid sample 16 is measured, is performed by use of the surface plasmon sensor 10 illustrated in FIG. 1 will be described hereinbelow.

Firstly, before the liquid sample 16 is introduced into the cup-shaped region of the dielectric material member 12, the laser beam source 20 is actuated, and a signal $S_{BASE}$, which represents the intensity of the reflected laser beam having been reflected from the interface between the dielectric material member 12 and the metal film 14, is acquired by use of the measuring detector 34. The signal $S_{BASE}$ is the base line signal corresponding to the intensity of the entire area of the incident laser beam, which has the Gaussian beam cross-sectional intensity distribution, in the state in which the attenuated total reflection due to the surface plasmon resonance does not occur.

Thereafter, the liquid sample 16 is introduced into the cup-shaped region of the dielectric material member 12 and brought into contact with the metal film 14. In this state, the laser beam source 20 is actuated, and a signal $S_{ATR}$, which represents the intensity of the reflected laser beam having been reflected from the interface between the dielectric material member 12 and the metal film 14, is acquired by use of the measuring detector 34. The signal $S_{ATR}$ is the signal corresponding to the intensity of the entire area of the reflected laser beam in the state in which the attenuated total reflection has occurred at part of the aforesaid base line signal $S_{BASE}$ corresponding to a specific incidence angle. (The signal $S_{ATR}$ is the signal obtained from integration of the beam cross-sectional intensity distribution, which is indicated by the solid line above the measuring detector 34 in FIG. 1.)

Thereafter, the signal processing section 36 calculates a difference signal $S_{BASE}-S_{ATR}$. Also, the signal processing section 36 specifies the incidence angle of a laser beam component, which has been subjected to the attenuated total reflection, in accordance with the value of the difference signal $S_{BASE}-S_{ATR}$ and takes the thus specified incidence angle as the ATR angle $\theta_{SP}$. Specifically, in this embodiment, the signal processing section 36 calculates a base line intensity B (illustrated in FIG. 1) corresponding to the part, at which the attenuated total reflection has occurred, on the assumption that the extent of the attenuated total reflection, i.e. the value of the difference signal $S_{BASE}-S_{ATR}$, will be equal to a value obtained from multiplication of the base line intensity B corresponding to the part, at which the attenuated total reflection has occurred, by a predetermined value. Also, the signal processing section 36 makes reference to a reference table, which has been prepared previously and represents a relationship between the base line intensity and the incidence angle. The signal processing section 36 thus specifies the incidence angle, which is associated with the occurrence of the attenuated total reflection, i.e. the ATR angle $\theta_{SP}$. With the processing described above, the ATR angle $\theta_{SP}$ is capable of being measured accurately by use of the low-cost, simple apparatus constitution, wherein the single measuring detector 34 for outputting the signal, which represents the intensity of the entire area of the light received by the measuring detector 34, is secured and located such that the measuring detector 34 is capable of receiving the reflected laser beam. Also, the calculation processing performed by the signal processing section 36 is markedly simple. Therefore, the measurement of the ATR angle $\theta_{SP}$ of the sample is capable of being performed with the low-cost, low-load processing.

In the embodiment of FIG. 1, the measuring detector 34 receives the entire area of the reflected laser beam. Alternatively, the measuring detector 34 may be secured and located such that the measuring detector 34 receives only a certain region contained in the entire area of the reflected laser beam. For example, the measuring detector 34 may be secured and located so as to receive only a region of the laser beam having been reflected from the interface described above, the region corresponding to one side of the Gaussian beam cross-sectional intensity distribution, which one side is presumed as containing the part associated with the occurrence of the attenuated total reflection.

Figure 2:
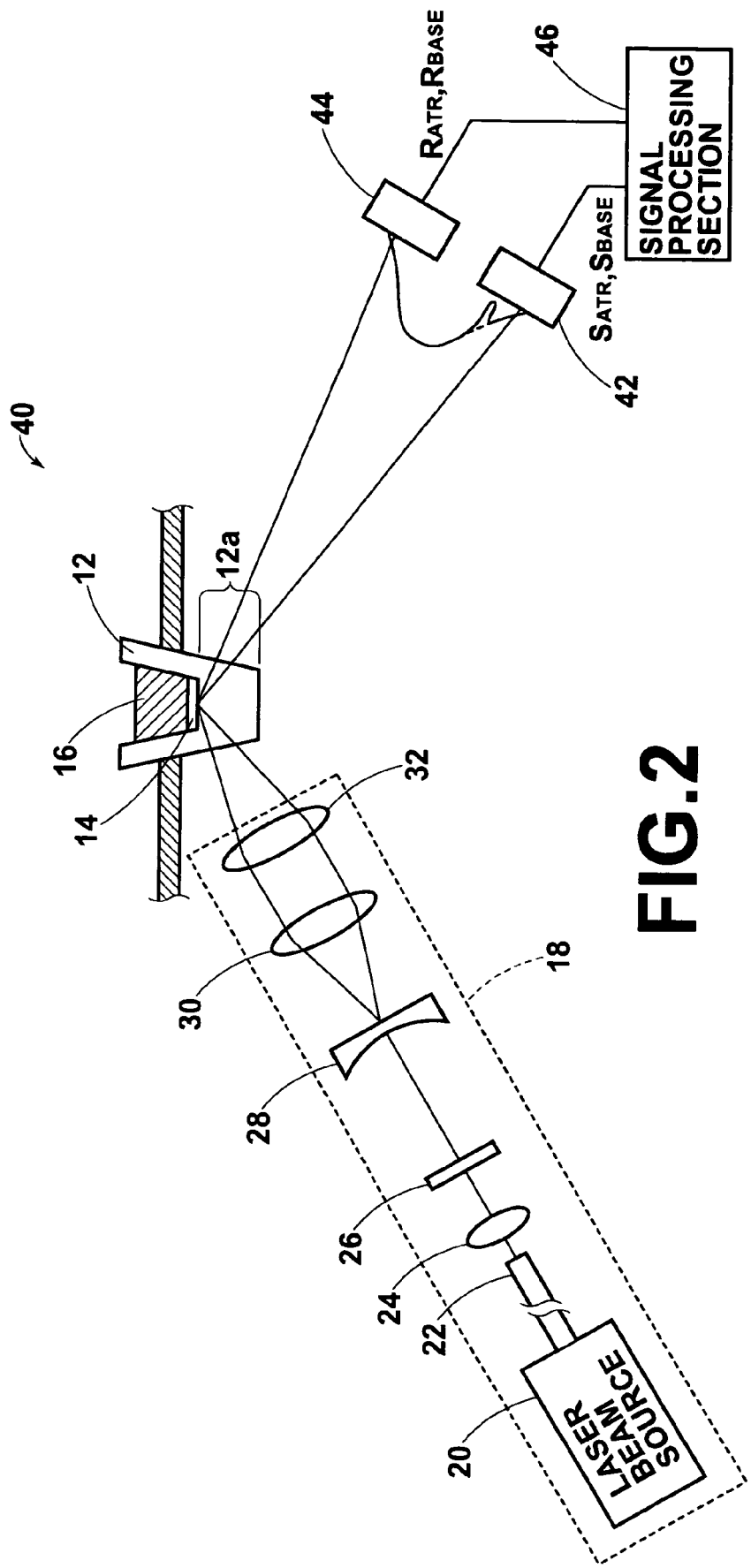
FIG. 2 is a side view showing a second embodiment of the sample analysis apparatus in accordance with the present invention, which is constituted as a surface plasmon sensor.

A second embodiment of the sample analysis apparatus in accordance with the present invention, which is constituted as a surface plasmon sensor 40, will be described hereinbelow with reference to FIG. 2. FIG. 2 is a side view showing the surface plasmon sensor 40. In FIG. 2 (and those that follow), similar elements are numbered with the same reference numerals with respect to FIG. 1.

The surface plasmon sensor 40 illustrated in FIG. 2 has a constitution basically identical with the constitution of the surface plasmon sensor 10 illustrated in FIG. 1, except that, in lieu of the measuring detector 34, a measuring detector 42 and a light intensity monitoring detector 44 are provided. The measuring detector 42 and the light intensity monitoring detector 44 are connected to a signal processing section 46. Each of the measuring detector 42 and the light intensity monitoring detector 44 is a single detector, which is secured and located for light detection. Each of the measuring detector 42 and the light intensity monitoring detector 44 outputs a signal, which represents the intensity of the entire area of the received light, into the signal processing section 46. The measuring detector 42 is secured and located so as to receive only the region of the laser beam having been reflected from the interface between the dielectric material member 12 and the metal film 14, the region corresponding to one side of the Gaussian beam cross-sectional intensity distribution, which one side is presumed as containing the part associated with the occurrence of the attenuated total reflection. The light intensity monitoring detector 44 is secured and located so as to receive only the region of the laser beam having been reflected from the interface between the dielectric material member 12 and the metal film 14, the region corresponding to the other side opposite to the aforesaid one side of the Gaussian beam cross-sectional intensity distribution. Each of the measuring detector 42 and the light intensity monitoring detector 44 may be a single-cell type of detector. Alternatively, each of the measuring detector 42 and the light intensity monitoring detector 44 may be a multi-cell type of detector, such as a CCD sensor, which is utilized so as to output an integration signal representing the total intensity of the light received by all of the cells.

How an analysis, in which the ATR angle $\theta_{SP}$ of the liquid sample 16 is measured, is performed by use of the surface plasmon sensor 40 illustrated in FIG. 2 will be described hereinbelow.

Firstly, before the liquid sample 16 is introduced into the cup-shaped region of the dielectric material member 12, the laser beam source 20 is actuated, and a signal $S_{BASE}$, which represents the intensity of the region of the laser beam having been reflected from the interface between the dielectric material member 12 and the metal film 14, the region corresponding to the aforesaid one side of the Gaussian beam cross-sectional intensity distribution, is acquired by use of the measuring detector 42. At the same time, a signal $R_{BASE}$, which represents the intensity of the region of the laser beam having been reflected from the interface between the dielectric material member 12 and the metal film 14, the region corresponding to the other side opposite to the aforesaid one side of the Gaussian beam cross-sectional intensity distribution, is acquired by use of the light intensity monitoring detector 44.

Thereafter, the liquid sample 16 is introduced into the cup-shaped region of the dielectric material member 12 and brought into contact with the metal film 14. In this state, the laser beam source 20 is actuated, and a signal $S_{ATR}$, which represents the intensity of the region of the laser beam having been reflected from the interface between the dielectric material member 12 and the metal film 14, the region corresponding to the aforesaid one side of the Gaussian beam cross-sectional intensity distribution, is acquired by use of the measuring detector 42. At the same time, a signal $R_{ATR}$, which represents the intensity of the region of the laser beam having been reflected from the interface between the dielectric material member 12 and the metal film 14, the region corresponding to the other side opposite to the aforesaid one side of the Gaussian beam cross-sectional intensity distribution, is acquired by use of the light intensity monitoring detector 44.

Thereafter, the signal processing section 46 calculates a normalized signal $S_{BASE}/R_{BASE}$ and a normalized signal $S_{ATR}/R_{ATR}$. Also, the signal processing section 46 calculates a difference signal $(S_{BASE}/R_{BASE})-(S_{ATR}/R_{ATR})$, which represents the difference between the normalized signal $S_{BASE}/R_{BASE}$ and the normalized signal $S_{ATR}/R_{ATR}$. Further, the signal processing section 46 specifies the incidence angle of the laser beam component, which has been subjected to the attenuated total reflection, in accordance with the value of the difference signal $(S_{BASE}/R_{BASE})-(S_{ATR}/R_{ATR})$ and takes the thus specified incidence angle as the ATR angle $\theta_{SP}$. Specifically, in this embodiment, the signal processing section 46 calculates a normalized base line intensity corresponding to the part, at which the attenuated total reflection has occurred, on the assumption that the extent of the attenuated total reflection, i.e. the value of the difference signal $(S_{BASE}/R_{BASE})-(S_{ATR}/R_{ATR})$, will be equal to a value obtained from multiplication of the normalized base line intensity corresponding to the part, at which the attenuated total reflection has occurred, by a predetermined value. Also, the signal processing section 46 makes reference to a reference table, which has been prepared previously and represents a relationship between the normalized base line intensity and the incidence angle. The signal processing section 46 thus specifies the incidence angle, which is associated with the occurrence of the attenuated total reflection, i.e. the ATR angle $\theta_{SP}$. With the processing described above, the ATR angle $\theta_{SP}$ is capable of being measured accurately by use of the low-cost, simple apparatus constitution, wherein the single measuring detector 42 for outputting the signal, which represents the intensity of the entire area of the light received by the measuring detector 42, is secured and located such that the measuring detector 42 is capable of receiving the reflected laser beam. Also, the calculation processing performed by the signal processing section 46 is markedly simple. Therefore, the measurement of the ATR angle $\theta_{SP}$ of the sample is capable of being performed with the low-cost, low-load processing. Further, by the provision of the light intensity monitoring detector 44, of the quantity of the alteration occurring with the intensity of the reflected laser beam, which intensity is detected by the measuring detector 42, a quantity of alteration occurring due to a fluctuation in power of the laser beam source 20 is capable of being canceled. Only the quantity of the alteration occurring with the intensity of the reflected laser beam due to the attenuated total reflection is thus capable of being detected, and a more accurate analysis is thus capable of being made.

In the second embodiment described above, it is fixed which detector is the measuring detector and which detector is the light intensity monitoring detector. Alternatively, one of a plurality of detectors may be selectively utilized as the measuring detector in accordance with the presumed attenuated total reflection angle, and one of the remaining detectors may be utilized as the light intensity monitoring detector.

A third embodiment of the sample analysis apparatus in accordance with the present invention, which is constituted as a surface plasmon sensor 50, will be described hereinbelow with reference to FIG. 3, FIG. 4A, FIG. 4B, and FIG. 4C.

Figure 3:
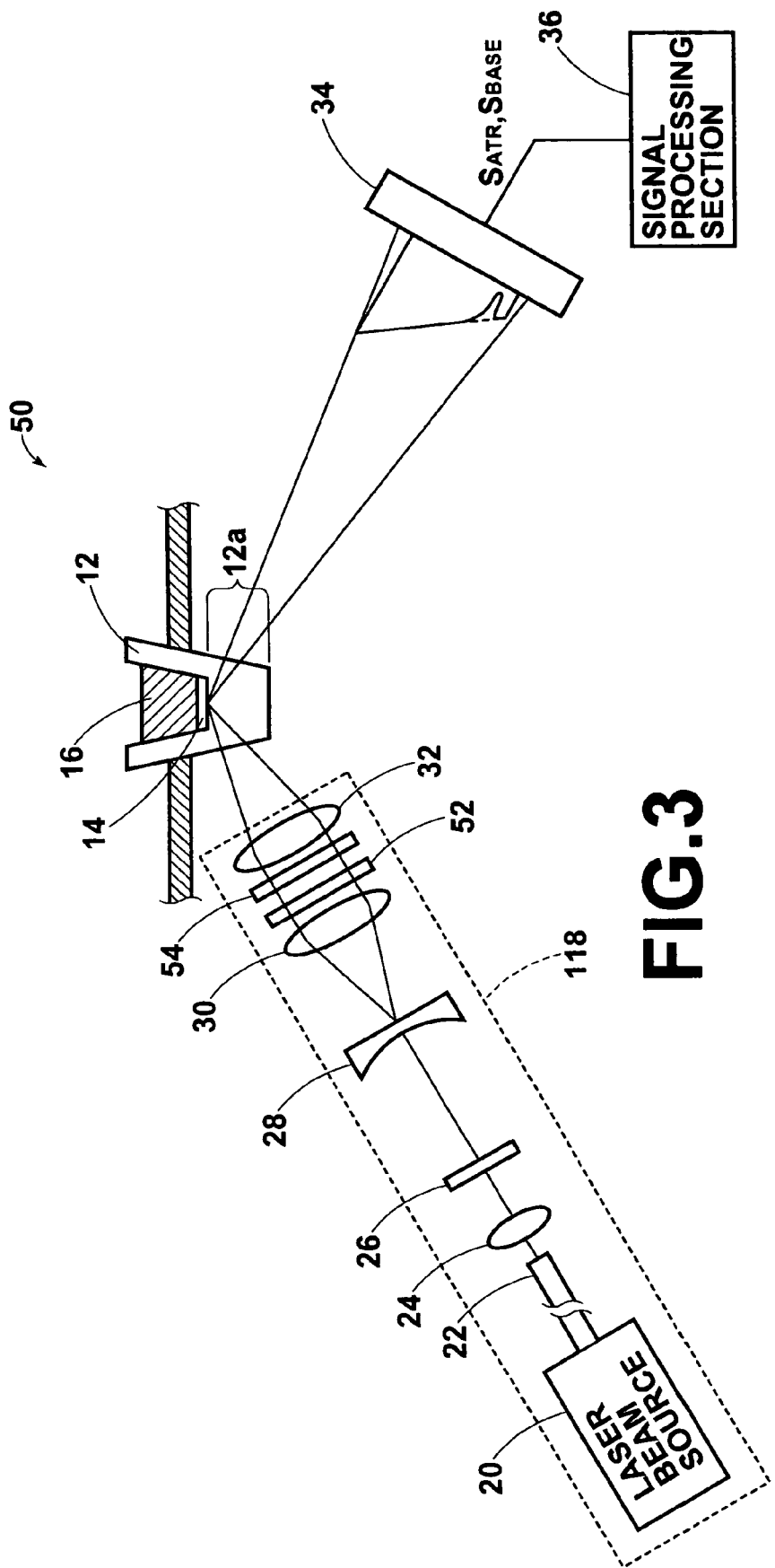
FIG. 3 is a side view showing a third embodiment of the sample analysis apparatus in accordance with the present invention, which is constituted as a surface plasmon sensor.
Figure 4A:
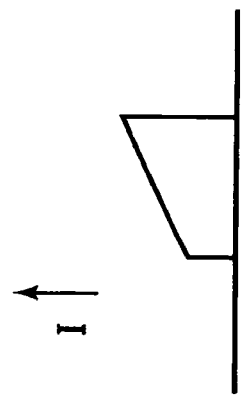
FIGS. 4A, 4B, and 4C are explanatory views showing how filters of a light beam irradiating optical system of the surface plasmon sensor of FIG. 3 operate.
Figure 4B:
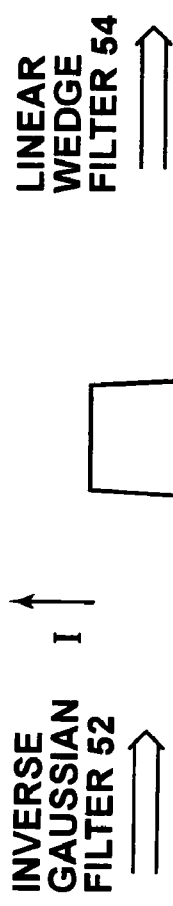
Figure 4C:
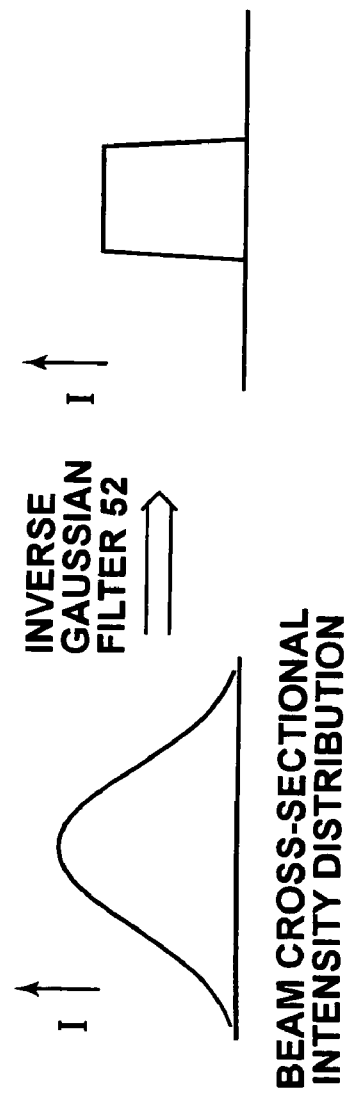

FIG. 3 is a side view showing the surface plasmon sensor 50. The surface plasmon sensor 50 has a constitution basically identical with the constitution of the surface plasmon sensor 10 illustrated in FIG. 1, except that, in lieu of the light beam irradiating optical system 18, a light beam irradiating optical system 118 is employed. In the light beam irradiating optical system 118, an inverse Gaussian filter 52 and a linear wedge filter 54 are located in the optical path between the converging lens 30 and the converging lens 32, at which optical path the laser beam has been collimated. As illustrated in FIG. 4A, FIG. 4B, and FIG. 4C, with the combination of the inverse Gaussian filter 52 and the linear wedge filter 54, the laser beam before impinging upon the interface between the dielectric material member 12 and the metal film 14 is converted into a laser beam having beam cross-sectional intensities, which monotonously increase or monotonously decrease in accordance with the incidence angles, in an incidence plane of a middle beam of the laser beam with respect to the interface between the dielectric material member 12 and the metal film 14. As a result, the base line intensity of the laser beam in the incidence plane monotonously increases or monotonously decreases in accordance with the incidence angles. Therefore, the incidence angle (i.e., the ATR angle $\theta_{SP}$) of the laser beam component, which has been subjected to the predetermined proportion of the attenuated total reflection with respect to the base line intensity, is capable of being specified more easily.

A fourth embodiment of the sample analysis apparatus in accordance with the present invention, which is constituted as a surface plasmon sensor 60, will be described hereinbelow with reference to FIG. 5.

Figure 5:
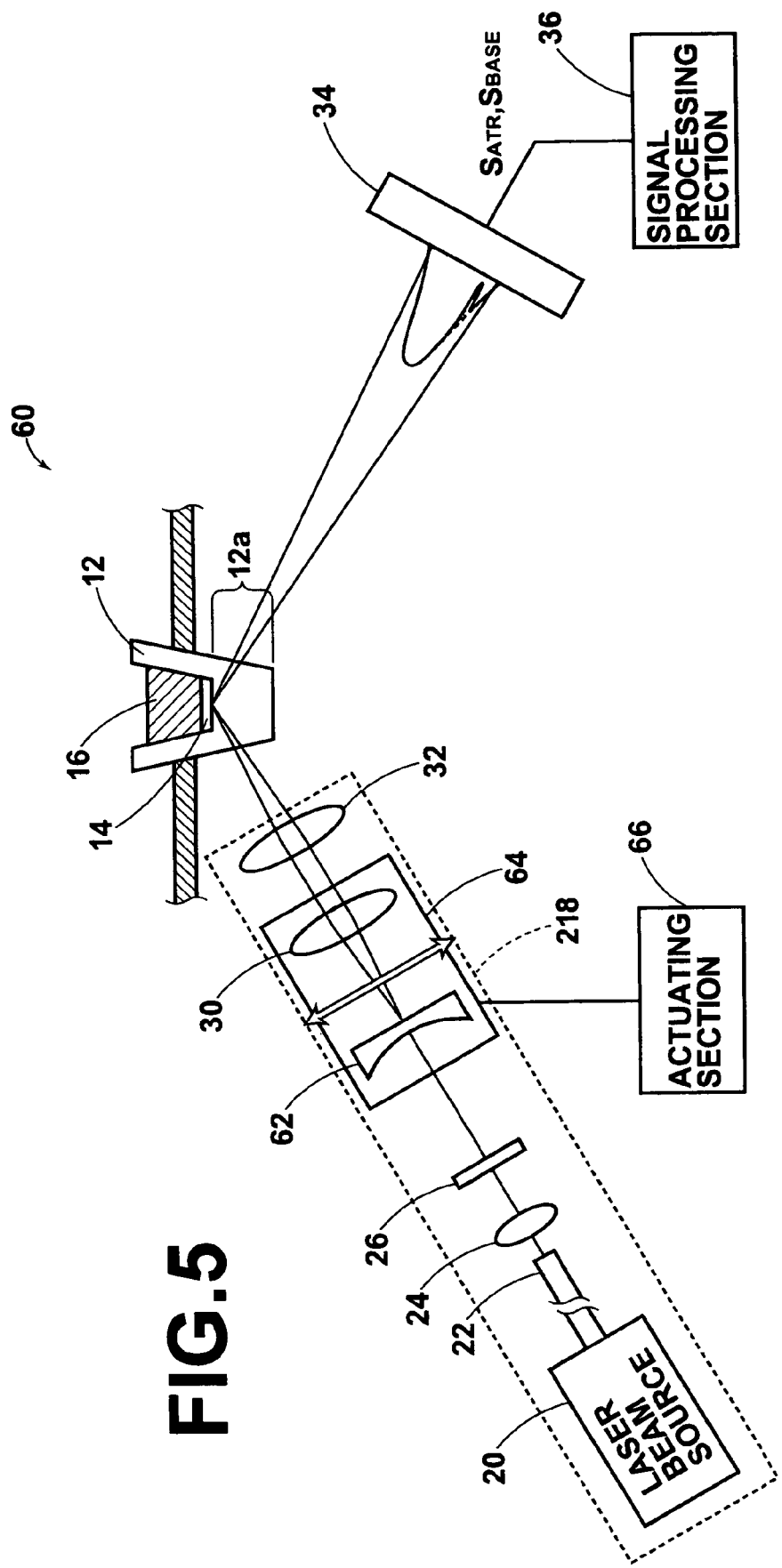
FIG. 5 is a side view showing a fourth embodiment of the sample analysis apparatus in accordance with the present invention, which is constituted as a surface plasmon sensor.

FIG. 5 is a side view showing the surface plasmon sensor 60. The surface plasmon sensor 60 has a constitution basically identical with the constitution of the surface plasmon sensor 10 illustrated in FIG. 1, except that, in lieu of the light beam irradiating optical system 18, a light beam irradiating optical system 218 is employed. In the light beam irradiating optical system 218, a diverging lens 62, which has a refractive power smaller than the refractive power of the diverging lens 28 of the light beam irradiating optical system 18, is employed. Also, the light beam irradiating optical system 218 is associated with an actuating section 66 for moving a part 64 of the light beam irradiating optical system 218, which part contains the diverging lens 62 and the converging lens 30, in a direction normal to the optical axis. Since the refractive power of the diverging lens 62 is small, the range of the incidence angles, which the laser beam impinging upon the interface between the dielectric material member 12 and the metal film 14 embraces, is narrower than the range of the incidence angles in the cases of the surface plasmon sensor 10 illustrated in FIG. 1. Also, the beam diameter of the reflected laser beam at the time, at which the reflected laser beam impinges upon the measuring detector 34, is smaller than the beam diameter of the reflected laser beam at the time, at which the reflected laser beam impinges upon the measuring detector 34, in the cases of the surface plasmon sensor 10 illustrated in FIG. 1. As a result, the gradient of the base line intensity of the laser beam at the time, at which the laser beam impinges upon the measuring detector 34, becomes large. Therefore, the quantity of the alteration occurring with the signal $S_{ATR}$ with respect to an alteration of the ATR angle $\theta_{SP}$ becomes large. Accordingly, the measurement of the ATR angle $\theta_{SP}$ is capable of being made with a high sensitivity. However, in such cases, since the range of the incidence angles, which the laser beam impinging upon the interface between the dielectric material member 12 and the metal film 14 embraces, becomes narrow, the part 64 of the light beam irradiating optical system 218 is set to be capable of being moved by the actuating section 66, such that the range of the ATR angle $\theta_{SP}$ capable of being measured may be kept wide. The range of the incidence angles, which the laser beam impinging upon the interface between the dielectric material member 12 and the metal film 14 embraces, is thus capable of being altered in accordance with the ATR angle $\theta_{SP}$ to be measured. In the fourth embodiment of FIG. 5, only the part 64 of the light beam irradiating optical system 218 is moved. Alternatively, the entire system of the light beam irradiating optical system 218 containing the laser beam source 20 may be moved.

A fifth embodiment of the sample analysis apparatus in accordance with the present invention, which is constituted as a surface plasmon sensor 70, will be described hereinbelow with reference to FIG. 6.

Figure 6:
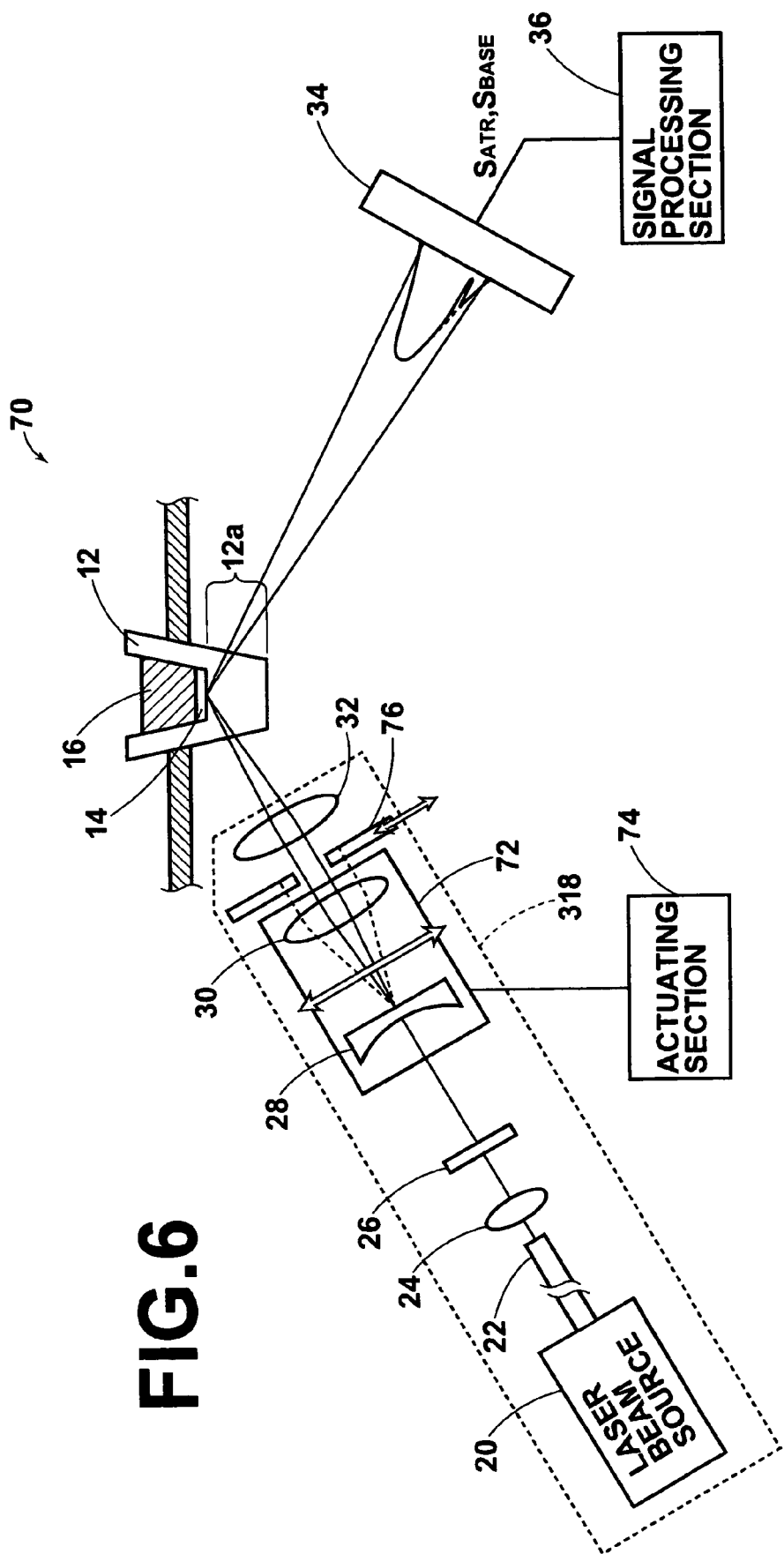
FIG. 6 is a side view showing a fifth embodiment of the sample analysis apparatus in accordance with the present invention, which is constituted as a surface plasmon sensor.

FIG. 6 is a side view showing the surface plasmon sensor 70. The surface plasmon sensor 70 has a constitution basically identical with the constitution of the surface plasmon sensor 10 illustrated in FIG. 1, except that, in lieu of the light beam irradiating optical system 18, a light beam irradiating optical system 318 is employed. The light beam irradiating optical system 318 is associated with an actuating section 74 for moving a part 72 of the light beam irradiating optical system 318, which part contains the diverging lens 28 and the converging lens 30, in a direction normal to the optical axis. Also, the light beam irradiating optical system 318 is provided with an aperture plate 76, which is capable of being inserted into the light beam irradiating optical system 318 in the direction normal to the optical axis. With the surface plasmon sensor 70, at an initial stage, the aperture plate 76 is not inserted into the light beam irradiating optical system 318, and the ATR angle $\theta_{SP}$ is approximately ascertained by use of a large-diameter laser beam having a beam cross-sectional intensity distribution, which has a gentle gradient. Thereafter, the part 72 of the light beam irradiating optical system 318 is moved, and the position of the laser beam is matched with the position corresponding to the approximately ascertained ATR angle $\theta_{SP}$. Also, the aperture plate 76 is inserted into the light beam irradiating optical system 318, and the ATR angle $\theta_{SP}$ is thus capable of being measured more accurately by use of a small-diameter laser beam, which has a sharp beam cross-sectional intensity distribution. In the fifth embodiment of FIG. 6, the aperture plate 76 is employed as the means for altering the beam diameter of the laser beam. Alternatively, for example, the laser beam source 20 may be provided with a switch for altering the beam diameter of the laser beam, and the switch may be utilized as the means for altering the beam diameter of the laser beam.

A sixth embodiment of the sample analysis apparatus in accordance with the present invention, which is constituted as a surface plasmon sensor 80, will be described hereinbelow with reference to FIG. 7.

Figure 7:
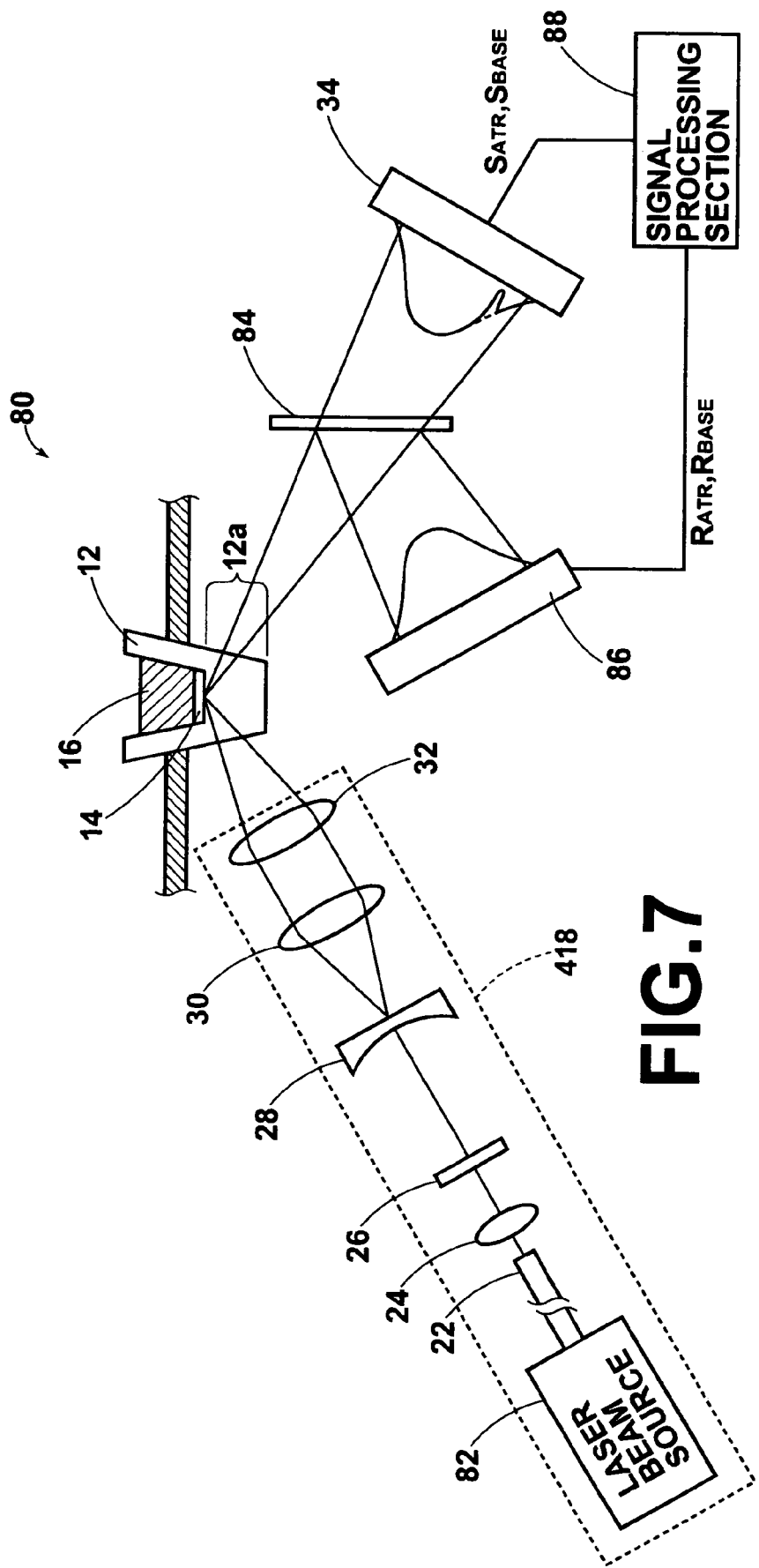
FIG. 7 is a side view showing a sixth embodiment of the sample analysis apparatus in accordance with the present invention, which is constituted as a surface plasmon sensor.

FIG. 7 is a side view showing the surface plasmon sensor 80. The surface plasmon sensor 80 has a constitution basically identical with the constitution of the surface plasmon sensor 10 illustrated in FIG. 1, except that a light beam irradiating optical system 418 is employed in lieu of the light beam irradiating optical system 18, the surface plasmon sensor 80 is further provided with a polarization beam splitter 84 and a light intensity monitoring detector 86, and a signal processing section 88 is employed in lieu of the signal processing section 36. The light beam irradiating optical system 418 is provided with a laser beam source 82 for producing a laser beam constituted of an S-polarized light beam and a P-polarized light beam, which are mixed together in a predetermined ratio. The polarization beam splitter 84 splits the laser beam, which has been reflected from the interface between the dielectric material member 12 and the metal film 14, into the S-polarized light beam and the P-polarized light beam. The polarization beam splitter 84 is located such that only the P-polarized light beam is capable of being received by the measuring detector 34. The light intensity monitoring detector 86 receives the S-polarized light beam having been split from the reflected laser beam and outputs a signal, which represents the intensity of the S-polarized light beam. Both the measuring detector 34 and the light intensity monitoring detector 86 are connected to the signal processing section 88.

In each of the first to fifth embodiments described above, the polarizing plate 26 is set at an angle for the extraction of only the P-polarized light beam. In the sixth embodiment of FIG. 7, the polarizing plate 26 is set at an angle, which is inclined by 20° C. to 30° C. from the angle of the polarizing plate 26 in each of the first to fifth embodiments described above. As the laser beam source 82, for example, a superluminescent diode (SLD) capable of producing the laser beam constituted of the S-polarized light beam and the P-polarized light beam, which are mixed together in a ratio of approximately 1:3, should preferably be employed. The processing performed by the signal processing section 88 is identical with the processing performed by the signal processing section 46 of the surface plasmon sensor 40 illustrated in FIG. 2. As described above, the attenuated total reflection occurs with respect to only the P-polarized light beam. Therefore, with the surface plasmon sensor 80 having the constitution described above, the light intensity of the S-polarized light beam, which the light intensity monitoring detector 86 receives, is not affected by the 44 attenuated total reflection and reflects only the alteration in light intensity due to a fluctuation in power of the laser beam source 82, and the like. Accordingly, with the processing, wherein each of the signals obtained from the measuring detector 34 is divided by the corresponding one of the signals obtained from the light intensity monitoring detector 86, of the quantity of the alteration occurring with the intensity of the reflected laser beam, which intensity is detected by the measuring detector 34, a quantity of alteration occurring due to a fluctuation in power of the laser beam source 82 is capable of being canceled. Only the quantity of the alteration occurring with the intensity of the reflected laser beam due to the attenuated total reflection is thus capable of being detected, and a more accurate analysis is thus capable of being made.

Each of the first to sixth embodiments described above may be modified such that the light beam irradiating optical system and the detector are secured and located within a housing.

FIG. 8 is a side view showing a housing 92 provided with a surface plasmon sensor 90, which has a constitution similar to the constitution of the surface plasmon sensor 10 of FIG. 1. The surface plasmon sensor 90 is provided with a mirror 94 added in the optical path of the light beam irradiating optical system. Also, in the surface plasmon sensor 90, in lieu of the dielectric material member 12 illustrated in FIG. 1, which is formed as the integral body, a dielectric material member comprising a prism section 96 and a cup section 98, which are capable of being separated from each other, is employed. As illustrated in FIG. 8, the laser beam source 20, the polarization plane keeping fiber 22, the collimator lens 24, the polarizing plate 26, the mirror 94, the diverging lens 28, the converging lens 30, the converging lens 32, the prism section 96, and the measuring detector 34 are secured and located within the housing 92. A top surface of the prism section 96 is exposed to the exterior of the housing 92. The cup section 98 provided with the metal film 14 is releasably mounted on the top surface of the prism section 96. The dielectric material member, which comprises the prism section 96 and the cup section 98, and the metal film 14 together constitute a sample support section. The liquid sample 16 is capable of being accommodated in the cup section 98 of the sample support section, such that liquid sample 16 is capable of being brought into contact with the metal film 14. A refractive index matching liquid may be located between the prism section 96 and the cup section 98. The laser beam source 20 and the measuring detector 34, each of which is to be connected to electric wiring and an interface with respect to the exterior of the housing 92, are collectively located on the identical surface. Each of surface plasmon sensors having constitutions similar to the constitutions of the aforesaid second to sixth embodiments of the surface plasmon sensors may be accommodated within a housing in the same manner as that in the surface plasmon sensor 90. In cases where the components of the surface plasmon sensor are thus secured and located within the housing, the surface plasmon sensor becomes easy to process, and re-adjustments for alignment of optical devices need not be performed after the surface plasmon sensor has been moved to a different location.

In each of the first to sixth embodiments of the surface plasmon sensors in accordance with the present invention, after the intensity of the reflected laser beam has been detected in the state in which the liquid sample 16 is absent on the metal film 14, the processing for calculating the absolute value of the ATR angle $\theta_{SP}$ is performed. Alternatively, each of the first to sixth embodiments of the surface plasmon sensors in accordance with the present invention may be utilized in other different ways. For example, the sensing substance may be fixed to the top surface of the metal film 14, and a liquid sample containing a test body, which is capable of undergoing binding with the sensing substance, may be introduced onto the sensing substance having been fixed to the metal film 14. Also, the quantity of the alteration of the ATR angle $\theta_{SP}$ may then be measured, and the state of the binding of the test body with the sensing substance may be detected in accordance with the quantity of the alteration of the ATR angle $\theta_{SP}$. Further, the sample analysis apparatus in accordance with the present invention is not limited to the surface plasmon sensor and may be constituted as a leaky mode sensor, or the like.

Besides the embodiments described above, the sample analysis apparatus in accordance with the present invention may be embodied in various other ways.

What is claimed is:

1. A sample analysis apparatus, comprising:
   i) a light beam irradiating optical system associated with a dielectric material member having a surface, on which a thin film layer has been formed, a sample being capable of being brought into contact with a surface of the thin film layer,
   the light beam irradiating optical system producing a light beam and irradiating the light beam to an interface between the dielectric material member and the thin film layer in a first state, in which the sample is absent on the surface of the thin film layer, and irradiating the light beam to the interface between the dielectric material member and the thin film layer in a second state, in which the sample has been brought into contact with the surface of the thin film layer,
   the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface;
   ii) a single measuring detector for outputting a first measurement signal, which represents an intensity of an entire area of light irradiated in the first state received by the measuring detector and for outputting a second measurement signal, which represents an intensity of an entire area of the light irradiated in the second state received by the measuring detector, the measuring detector being secured and located such that the measuring detector is capable of receiving the light beam, which has been reflected from the interface between the dielectric material member and the thin film layer; and
   iii) a calculating means for calculating an incidence angle of a light beam component among the light beam components constituting the light beam, which light beam component has been subjected to attenuated total reflection, in accordance with a value of a difference signal representing a difference between the first measurement signal and the second measurement signal, the thus specified incidence angle being taken as the attenuated total reflection angle of the sample.

2. An apparatus as defined in claim 1 wherein the light beam irradiating optical system is provided with means for altering the range of the incidence angles, which the light beam embraces.

3. An apparatus as defined in claim 1 wherein the light beam irradiating optical system is provided with means for altering a beam diameter of the entire area of the light beam.

4. An apparatus as defined in claim 2 wherein the light beam irradiating optical system is provided with means for altering a beam diameter of the entire area of the light beam.

5. An apparatus as defined in claim 1 wherein the light beam, which is produced by the light beam irradiating optical system, has beam cross-sectional intensities, which monotonously increase or monotonously decrease in accordance with the incidence angles, in an incidence plane of a middle beam of the light beam with respect to the interface between the dielectric material member and the thin film layer.

6. An apparatus as defined in claim 1 wherein the light beam irradiating optical system produces the light beam by producing a beam, which has a Gaussian beam cross-sectional intensity distribution in a plane parallel with an incidence plane of a middle beam of the light beam with respect to the interface between the dielectric material member and the thin film layer, and converging or diverging the beam toward the interface between the dielectric material member and the thin film layer.

7. An apparatus as defined in claim 6 wherein the measuring detector is located so as to receive only a region of the light beam having been reflected from the interface between the dielectric material member and the thin film layer, which region corresponds to one side of the Gaussian beam cross-sectional intensity distribution.

8. An apparatus as defined in claim 1 wherein the light beam irradiating optical system and the measuring detector are secured and located within a housing, and
   a sample support section, which comprises the dielectric material member and the thin film layer, is formed at a first surface of the housing, such that the thin film layer is exposed to the exterior of the housing.

9. An apparatus as defined in claim 8 wherein the light beam irradiating optical system comprises a light source section, and
   the light source section and the measuring detector are secured and located on a second surface within the housing, which second surface is different from the first surface of the housing.

10. An apparatus as defined in claim 7 wherein the apparatus further comprises a light intensity monitoring detector for detecting an intensity of the whole or part of a remaining region of the light beam having been reflected from the interface between the dielectric material member and the thin film layer, which remaining region is other than the region received by the measuring detector.

11. An apparatus as defined in claim 1 wherein the light beam, which is produced by the light beam irradiating optical system, is constituted of a first polarized light beam and a second polarized light beam, which are mixed together in a predetermined ratio, and
   the apparatus further comprises:
   a polarization beam splitter for splitting the light beam, which has been reflected from the interface between the dielectric material member and the thin film layer, into the first polarized light beam and the second polarized light beam, the polarization beam splitter being located such that only the first polarized light beam is received by the measuring detector, and
   a light intensity monitoring detector for detecting an intensity of the whole or part of the second polarized light beam.

12. An apparatus as defined in claim 10 wherein the light beam irradiating optical system, the measuring detector, and the light intensity monitoring detector are secured and located within a housing, and
   a sample support section, which comprises the dielectric material member and the thin film layer, is formed at a first surface of the housing, such that the thin film layer is exposed to the exterior of the housing.

13. An apparatus as defined in claim 11 wherein the light beam irradiating optical system, the measuring detector, and the light intensity monitoring detector are secured and located within a housing, and
   a sample support section, which comprises the dielectric material member and the thin film layer, is formed at a first surface of the housing, such that the thin film layer is exposed to the exterior of the housing.

14. An apparatus as defined in claim 12 wherein the light beam irradiating optical system comprises a light source section, and the light source section, the measuring detector, and the light intensity monitoring detector are secured and located on a second surface within the housing, which second surface is different from the first surface of the housing.

15. An apparatus as defined in claim 13 wherein the light beam irradiating optical system comprises a light source section, and the light source section, the measuring detector, and the light intensity monitoring detector are secured and located on a second surface within the housing, which second surface is different from the first surface of the housing.

16. An analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, and ii) a single measuring detector for outputting a signal, which represents an intensity of an entire area of light received by the measuring detector, the measuring detector being secured and located such that the measuring detector is capable of receiving the light beam, which has been reflected from the interface between the dielectric material member and the thin film layer, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, being thereby obtained, and c) specifying an incidence angle of a light beam component among the light beam components constituting the light beam, which light beam component has been subjected to attenuated total reflection, in accordance with a value of a difference signal representing a difference between the first measurement signal and the second measurement signal, the thus specified incidence angle being taken as the attenuated total reflection angle of the sample.

17. An analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam irradiating optical system producing the light beam by producing a beam, which has a Gaussian beam cross-sectional intensity distribution in a plane parallel with an incidence plane of a middle beam of the light beam with respect to the interface between the dielectric material member and the thin film layer, and converging or diverging the beam toward the interface between the dielectric material member and the thin film layer, ii) a single measuring detector for outputting a signal, which represents an intensity of an entire area of light received by the measuring detector, the measuring detector being secured and located such that the measuring detector is capable of receiving only a region of the light beam having been reflected from the interface between the dielectric material member and the thin film layer, which region corresponds to one side of the Gaussian beam cross-sectional intensity distribution, and iii) a light intensity monitoring detector for detecting an intensity of the whole or part of a remaining region of the light beam having been reflected from the interface between the dielectric material member and the thin film layer, which remaining region is other than the region received by the measuring detector, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, and a first monitoring signal, which represents the intensity of the entire area of the light received by the light intensity monitoring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, and a second monitoring signal, which represents the intensity of the entire area of the light received by the light intensity monitoring detector, being thereby obtained, and c) specifying an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

18. An analysis method, wherein an attenuated total reflection angle of a sample is measured by use of a sample analysis apparatus comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam, which is produced by the light beam irradiating optical system, being constituted of a first polarized light beam and a second polarized light beam, which are mixed together in a predetermined ratio, ii) a polarization beam splitter for splitting the light beam, which has been reflected from the interface between the dielectric material member and the thin film layer, into the first polarized light beam and the second polarized light beam, iii) a single measuring detector for outputting a signal, which represents an intensity of an entire area of light received by the measuring detector, the measuring detector being secured and located such that the measuring detector is capable of receiving only the first polarized light beam, and iv) a light intensity monitoring detector for detecting an intensity of the whole or part of the second polarized light beam, the method comprising the steps of:

a) irradiating the light beam from the light beam irradiating optical system to the interface between the dielectric material member and the thin film layer in a state, in which the sample is absent on the surface of the thin film layer, a first measurement signal, which represents the intensity of the entire area of the light received by the measuring detector, and a first monitoring signal, which represents the intensity of the entire area of the light received by the light intensity monitoring detector, being thereby obtained, b) irradiating the light beam from the light beam irradiating optical system to the interface between the dielectric material member and the thin film layer in a state, in which the sample has been brought into contact with the surface of the thin film layer, a second measurement signal, which represents the intensity of the entire area of the light received by the measuring detector, and a second monitoring signal, which represents the intensity of the entire area of the light received by the light intensity monitoring detector, being thereby obtained, and c) specifying an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

19. The sample analysis apparatus of claim 1, wherein each of the light beam components reflected incident angle determines the type of sample.

20. The sample analysis apparatus of claim 1, wherein each reflected incident angle identifies the sample within a particular range of error.

21. The analysis method of claim 16, wherein each of the light beam components reflected incident angle determines the type of sample.

22. The sample analysis apparatus of claim 1, wherein the measuring detector detects a reference base line signal which occurs without surface plasmon resonance.

23. The sample analysis apparatus of claim 22, wherein the measuring detector detects a reference base line signal which corresponds to a specific incidence angle.

24. The sample analysis apparatus of claim 23, wherein a difference signal is equal to the base line signal multiplied by a predetermined value.

25. A sample analysis apparatus, comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer in a first state, in which the sample is absent on the surface of the thin film layer, and irradiating the light beam to the interface between the dielectric material member and the thin film layer in a second state, in which the sample has been brought into contact with the surface of the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam irradiating optical system producing the light beam by producing a beam, which has a Gaussian beam cross-sectional intensity distribution in a plane parallel with an incidence plane of a middle beam of the light beam with respect to the interface between the dielectric material member and the thin film layer, and converging or diverging the beam toward the interface between the dielectric material member and the thin film layer, ii) a single measuring detector for outputting a first measurement signal, which represents an intensity of an entire area of light irradiated in the first state received by the measuring detector and for outputting a second measurement signal, which represents an intensity of an entire area of the light irradiated in the second state received by the measuring detector, the measuring detector being secured and located such that the measuring detector is capable of receiving only a region of the light beam having been reflected from the interface between the dielectric material member and the thin film layer, which region corresponds to one side of the Gaussian beam cross-sectional intensity distribution, and iii) a light intensity monitoring detector for detecting a first monitoring signal, which represents an intensity of an entire area of light irradiated in the first state received by the light intensity monitoring detector and for outputting a second monitoring signal, which represents an intensity of an entire area of light irradiated in the second state received by the light intensity monitoring detector; and iv) a calculating means for calculating an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

26. A sample analysis apparatus, comprising:

i) a light beam irradiating optical system associated with a dielectric material member having a surface, on which a thin film layer has been formed, the sample being capable of being brought into contact with a surface of the thin film layer, the light beam irradiating optical system producing a light beam and irradiating the light beam to an interface between the dielectric material member and the thin film layer in a first state, in which the sample is absent on the surface of the thin film layer, and irradiating the light beam to the interface between the dielectric material member and the thin film layer in a second state, in which the sample has been brought into contact with the surface of the thin film layer, the light beam, which is produced by the light beam irradiating optical system, being constituted of light beam components, which have various different incidence angles with respect to the interface between the dielectric material member and the thin film layer, and which have intensities varying in accordance with the incidence angles with respect to the interface, the light beam, which is produced by the light beam irradiating optical system, being constituted of a first polarized light beam and a second polarized light beam, which are mixed together in a predetermined ratio, ii) a polarization beam splitter for splitting the light beam, which has been reflected from the interface between the dielectric material member and the thin film layer, into the first polarized light beam and the second polarized light beam, iii) a single measuring detector for outputting a first measurement signal, which represents an intensity of an entire area of light irradiated in the first state received by the measuring detector and for outputting a second measurement signal, which represents an intensity of an entire area of the light irradiated in the second state received by the measuring detector, the measuring detector being secured and located such that the measuring detector is capable of receiving only the first polarized light beam, iv) a light intensity monitoring detector for detecting a first monitoring signal, which represents an intensity of a whole or a part of the second polarized light beam irradiated in the first state received by the light intensity monitoring detector and for outputting a second monitoring signal, which represents an intensity of a whole or a part of the second polarized light beam irradiated in the second state received by the light intensity monitoring detector; and v) a calculating means for calculating an incidence angle of a light beam component among the light beam components constituting the light beam, which light beam component has been subjected to attenuated total reflection, in accordance with a value of a difference signal representing a difference between a signal, which is obtained from a division of the first measurement signal by the first monitoring signal, and a signal, which is obtained from a division of the second measurement signal by the second monitoring signal, the thus specified incidence angle being taken as the attenuated total reflection angle of the sample.

* * * * *